United States Patent [19]

Miller et al.

[11] Patent Number: 5,487,975
[45] Date of Patent: Jan. 30, 1996

[54] BIOTIN/AVIDIN FORMULATION

[75] Inventors: Phillip C. Miller; Roberta L. Druyor; Ralph R. Martel, all of Tucson, Ariz.

[73] Assignee: Ventana Medical Systems, Inc., Tucson, Ariz.

[21] Appl. No.: 152,864

[22] Filed: Nov. 15, 1993

[51] Int. Cl.$^6$ .................................................. G01N 33/535
[52] U.S. Cl. ........................ 435/7.5; 435/7.2; 435/7.21; 435/7.9; 435/960; 435/962; 435/967; 435/975
[58] Field of Search ................................. 435/7.5, 7.2, 28, 435/7.21, 7.9, 7.95, 962, 967, 975, 960; 436/503, 63; 424/3

[56] References Cited

U.S. PATENT DOCUMENTS

| | | | |
|---|---|---|---|
| 4,166,106 | 8/1979 | Sedlacek et al. | 435/7.21 |
| 4,818,686 | 4/1989 | Kortwright et al. | 435/7.21 |
| 4,954,617 | 9/1990 | Fanger et al. | 530/387 |
| 5,066,581 | 11/1991 | Suciu-Foca et al. | 435/7.24 |
| 5,225,325 | 7/1993 | Miller et al. | 435/6 |

OTHER PUBLICATIONS

Duhamel, R. C. et al. "Prevention of nonspecific binding of avidin." *Methods in Enzymology* 184:201–207, 1990.
Brandon, C., *Improved Immunocytochemical Staining Through the Use of Fab Fragments of Primary Antibody, Fab–specific Second Antibody, and Fab–Horseradish Peroxidase*, 33 The Journal of Histochemistry and Cytochemistry 715 (abstract) (1985).
Duhamel, R. and Johnson, D., *Use of Nonfat Dry Milk to Block Nonspecific Nuclear and Membrane Staining by Avidin Conjugates*, 33 The Journal of Histochemistry and Cytochemistry 711–714 (1985).
Hochhaus, G. and Sadée, W., *A Biotin–Avidin–Based Enzyme Immunoassay for $\beta_h$–Endorphin*, 5 Pharmaceutical Research 232–235 (1988).

*Primary Examiner*—David Saunders
*Attorney, Agent, or Firm*—Skjerven, Morrill, MacPherson, Franklin & Friel; Laura Terlizzi

[57] ABSTRACT

The present invention provides an improved biotin-avidin formulation in which a biotinylated antibody conjugate or an avidin-enzyme conjugate is present in a suitable diluent for immunohistochemical staining. The diluent additionally comprises casein in an amount sufficient to prevent charge interactions of the conjugate with a tissue section and gamma globulin in an amount sufficient to prevent Fc receptor binding and any hydrophobic interaction of the conjugate with a tissue section. In a preferred embodiment, the immunoglobulin is from the same species as the biotinylated antibody conjugate. The formulation effectively reduces overall unwanted binding, irrespective of the source of the binding.

14 Claims, No Drawings

BIOTIN/AVIDIN FORMULATION

FIELD OF THE INVENTION

This invention relates to a diluent used for biotin-avidin based immunohistochemical detection procedures that reduces nonspecific staining while maintaining specific staining.

BACKGROUND OF THE INVENTION

Biotin-avidin detection systems have been widely used in immunohistochemical staining procedures because of their versatility and the high binding affinity between biotin and avidin. Biotin can be conjugated to proteins such as antibodies, to lectins, and to nucleic acids. Avidin can be conjugated to fluorochromes and enzymes with minimal loss of activity.

However, a major drawback to using biotin-avidin detection systems in immunohistochemistry is the endogenous avidin-binding ability of many tissues and non-specific binding of biotin derivatized proteins and avidin conjugated proteins. Many tissues contain endogenous biotin-containing macromolecules which contribute to a specific but undesired binding. This specific binding can be blocked using a sequential addition of excess avidin followed by excess biotin (G. S. Wood and R. Warnke, *J. Histochem. Cytochem.* 29:1196, 1981). An additional problem is the non-specific binding of avidin, which is due to a number of poorly defined mechanisms which are probably related to ionic and or hydrophobic protein-protein or protein-substrate interactions. For example, avidin-horseradish peroxidase conjugates have been observed to bind to cellular components in liver and kidney, but not in skin, lymph node, or spleen. Heparin in mast cells treated with certain fixatives can bind avidin ionically. In addition, some commercial lots of avidin exhibit non-specific binding with chromatin while other lots do not.

To date, no one means of blocking the unwanted binding is suitable. For each type of unwanted binding, the cellular component or tissue type associated with the binding dictates the preferred method of eliminating the unwanted binding. See for example, Duhamel et al, Methods in Enzymology 184:201–207 (1990) which describes methods of blocking unwanted binding based on the source and tissue type of the binding.

Many of the methods used to block unwanted binding are non-systematic such as use of whole serum which limits the reproducibility of the method. A defined medium that could block any source of unwanted biotin-avidin binding irrespective of the tissue being immunostained would eliminate the major drawback to use of biotin-avidin detection systems in immunohistochemistry.

SUMMARY OF THE INVENTION

The present invention provides an improved biotin-avidin formulation in which a biotinylated antibody conjugate or an avidin-enzyme conjugate is present in a suitable diluent for immunohistochemical staining. The diluent additionally comprises casein in an amount sufficient to prevent charge interactions of the conjugate with a tissue section and gamma globulin in an amount sufficient to prevent Fc receptor binding and any hydrophobic interaction of the conjugate with a tissue section. In a preferred embodiment, the immunoglobulin is from the same species as the biotinylated antibody conjugate. The formulation effectively reduces overall unwanted binding, irrespective of the source of the binding.

DESCRIPTION OF THE INVENTION

The present invention provides an improved biotin-avidin formulation that eliminates unwanted binding in biotin-avidin detection systems. The formulation comprises either a biotinylated antibody conjugate or an avidin-enzyme conjugate in a suitable diluent for immunohistochemical staining. The diluent additionally comprises the combination of casein and gamma globulin which effectively reduces overall unwanted binding, irrespective of the source of the binding.

Biotinylated Antibody Conjugate

A biotinylated antibody conjugate of this invention does not differ from prior art biotinylated antibody conjugates. As is well known, a primary antibody is specific for the antigen of interest. A secondary antibody is specific for the primary antibody and is labeled. In biotin-avidin detection systems, the secondary antibody is labeled with biotin. In a preferred embodiment, the primary antibody is a mouse monoclonal antibody or a rabbit polyclonal antibody. Preferred antibodies of the biotinylated antibody conjugate are goat anti-mouse immunoglobulin antibodies and goat anti-rabbit immunoglobulin antibodies. Most preferred antibodies of the biotinylated antibody conjugate are goat anti-mouse IgG antibodies, goat anti-mouse IgM antibodies, and goat anti-rabbit IgG antibodies. The antibodies can be intact or can be fragments of antibodies such as the $(Fab')_2$ fraction of the antibody.

The biotinylated antibody conjugate is preferably present in the diluent at the working dilution of the antibody.

Avidin-Enzyme Conjugate

An avidin-enzyme conjugate of this invention does not differ from prior art avidin-enzyme conjugates. As is well known, in biotin-avidin detection systems, the avidin of the avidin-enzyme conjugate binds to the biotin of the biotinylated antibody conjugate, providing an enzyme label for all the biotinylated antibodies. The enzyme is used to break down an enzyme substrate, either eliminating or, in most cases, creating a chromophore. In a preferred embodiment, the enzyme of the avidin-enzyme conjugate is horseradish peroxidase, alkaline phosphatase or beta-galactosidase.

The avidin-enzyme conjugate is preferably present in the diluent at the working dilution of the antibody.

Diluent

With the exception of the addition of casein and immunoglobulin, the conjugate diluent of this invention does not differ from prior art diluents. The diluent includes a physiologic buffer which is suitable for immunochemical procedures. Suitable buffers include the physiologic buffers such as Tris buffer, phosphate buffer (PB), citrate buffer, phosphate buffered saline (PBS). The diluent buffer is preferably the buffer used in the immunochemical staining procedure. A most preferred buffer for the diluent is PBS (0.1M phosphate buffer, 0.15M NaCl, pH 7.3).

The buffer optionally also includes a detergent and a preservative when used in the staining procedure. The detergent is in an amount sufficient to reduce surface tension of the solution to provide for even sheeting of the buffer to ensure that the entire tissue section is effectively covered by the antibody solution. Suitable detergents are those which are compatible with immunohistochemical staining reagents and immunochemical reagents in general and can be any of the nonionic biological detergents used by biochemists for the solubilization of proteins and membrane components. Polyoxyethylenesorbitans and polyoxyethylene ethers are preferred. More preferred is polyoxyethylenesorbitan monolaurate (sold under the name Tween 20) and polyoxyethylene 23 lauryl ether (sold under the name Brij 35). Both detergents are available from a variety of sources including Sigma Chemical Co. St. Louis, MO. The detergent is generally used at a concentration of about 0.01 to about 5% (v/v), more preferably at about 0.05 to about 1% (v/v), most preferably at about 0.05 to about 0.5% (v/v). (As used herein unless otherwise specified, % means weight percent which is the number of grams in 100 ml total volume.)

The diluent can also include a preservative such as an antimycotic or antimicrobial agent in an effective concentration to inhibit growth of microorganisms in the solution. Preservatives which do not interfere with immunochemical reactions are well known. Exemplary agents are gentamycin, penicillin, streptomycin, thimerosal, and, preferably, a mixture of 2-chloro-2-methyl- 4-isothiazolin-3-one, 2-methyl-4-isothiozolin-3-one and triethylorthoformate in dipropylene glycol available commercially under the product name PROCLIN 300 from Supelco, Inc., Bellefonte, Pa.

Sodium azide is known to inactivate peroxidase enzyme activity and is preferably not used with peroxidase staining reagents. The agents are effective at concentrations in the range of about 0.001% to 0.1% and are preferably used at about 0.01 to about 0.1%, more preferably about 0.05%.

A most preferred diluent is PBS, pH 7.3 containing 0.06% BRIJ 35 detergent and 0.05% PROCLIN 300 antimicrobial. When the conjugate is a biotinylated antibody, the diluent preferably also has 0.01M EDTA (ethylene diamine tetraacetic acid).

Gamma Globulin

The conjugate diluent of this invention additionally contains gamma globulin. Gamma globulin is the globulin fraction of nonimmune serum. Preferably the gamma globulin is of the species of the biotinylated antibody. Conveniently, the gamma globulin is the globulin fraction of goat serum.

The globulin fraction can be prepared from nonimmune serum by using saturated ammonium sulfate. Alternatively, more purified globulin fractions, such as produced by DEAE cellulose purification (similar to Cohn's fraction II) can also be used. Most preferred is Cohn's fraction II/III which can be prepared by well known methods and is commercially available from a number of sources including Sigma Chemical Co. (cat. no. G 5640).

The gamma globulin is present in the diluent in an amount sufficient to prevent Fc receptor binding and any hydrophobic interaction of the conjugate with a tissue section. Preferably, the concentration is from about 0.1% to about 5%, more preferably about 0.3% (or 3 mg/ml).

Casein

The conjugate diluent of this invention additionally contains casein. Casein is a mixture of proteins precipitated from milk with acid or by the action of rennin. The casein can be from a number of sources and is conveniently bovine.

Standard preparations of casein are suitable. More purified fractions are also suitable. A most preferred casein is a purified powder obtained from bovine milk by precipitation with hydrochloric acid.

Casein is present in the formulation in an amount sufficient to prevent charge interactions of the conjugate with a tissue section. Preferably, casein is present at a concentration of from about 5 mg/ml to about 30 mg/ml, more preferably, from about 10 mg/ml to about 15 mg/ml, most preferably about 12 mg/ml.

Using the Biotin Avidin Formulations

A biotin-avidin conjugate formulation of this invention is used in the same manner as the if conjugate were diluted in a prior art formulation. The immunochemical procedure differs in that a nonimmune serum blocking step can be eliminated, as discussed below.

The use of gamma globulin and casein improves the blocking of binding due to the endogenous avidin-binding ability of many tissues and non-specific binding of biotin and avidin. The combination of gamma globulin and casein minimizes avidin ionic interactions which causes binding to cellular component and avidin's non-specific binding with chromatin. In addition, the blocking is effective irrespective of the source of the unwanted binding, the tissue type, the fixative, if any, with which the tissue was treated and the nature of the nonspecific binding. The blocking of unwanted binding is systematic, and therefore, unlike use of whole serum, is reproducible.

This invention is further illustrated by the following specific but non-limiting examples. Procedures which are constructively reduced to practice are described in the present tense, and procedures which have been carried out in the laboratory are set forth in the past tense.

EXAMPLE 1

Preparation of Diluent for Biotinylated Antibodies

A preferred diluent of this invention was prepared as follows. The stock concentrate casein solution was prepared as follows.

Add 670 ml room temperature deionized water to a suitable glass container. Add the 80 g of solid casein (from bovine milk purified powder; Sigma Chemical Co. Catalog No. C-5890), while stirring. Stir vigorously until the casein is thoroughly suspended. Add 61.3 ml of 1N NaOH. Add, while stirring, 330 ml of hot (>90° C.) deionized water. While stirring, heat the suspension to >90° C. Once the temperature of the solution is over 90 degrees Celsius, continue to heat the solution, while stirring, for 15 to 30 minutes. Cool solution, while stirring, to room temperature. Adjust the volume of the solution to 1 liter (L) with deionized water. Filter the solution through a 1.2 μm serum filter. Filter the solution through a 0.45 μm filter cartridge. Calculate filtration loss as percent yield. Using 1:10 serial dilutions, prepare five (5) 1:100 dilutions of the casein solution in distilled water. Measure the absorbance versus distilled water of the 1:100 dilutions at 280 nm on a spectrophotometer. Calculate the average absorbance at 280 nm and use that value to determine the final concentration of the casein, using 1 $(mg/ml)^{-1}cm^{-1}$ as the conversion factor. Store at 2°–8° C. The shelf life is about 2 weeks.

The diluent for biotinylated antibodies was prepared as described below.

To prepare 1 L, place 600 ml of deionized water in a suitably sized container, and add in succession and with continuous mixing: 17.57 g dibasic potassium phosphate trihydrate, 2.76 g anhydrous monobasic sodium phosphate, 2.57 g of sodium chloride, 1.72 g 30% BRIJ 35 surfactant solution (Sigma Chemical Co., Catalog No. 430AG-6), 3.58 g trisodium EDTA. Mix until the solid is dissolved, then for an additional 5 minutes.

Next, add the required quantity of the stock concentrate casein solution to provide a final concentration of 13.4 mg/ml casein. Add 3 g goat globulins, 0.5 ml PROCLIN 300 antibiotic (Supelco, Catalog No. 4-8128). Mix until the solid is dissolved, then for an additional 30 minutes. Adjust volume to 950 ml with deionized water. Mix for 5 minutes and measure the pH.

The final pH should be 7.3±0.1. If pH differs from 7.3 by more than 0.2, review all additions and adjust with 6 N HCl if pH is above the desired value or 6N NaOH if pH is less than the desired value. If pH is adjusted, remix for an additional thirty minutes before measuring final pH.

Adjust to 1 L with deionized water, stir for five minutes, and record final pH. Use new tubing filter solution throughout a 0.2 μm SUPOR DCF filter (Gelman Sciences, Ann Arbor, Mich.), and visually inspect for appearance. Solution should be light amber in color and translucent. Calculate filtration loss as percent yield. Store at 2°–8° C.

EXAMPLE 2

Preparation of Diluent for Avidin-Enzyme Conjugates

The diluent for avidin-enzyme conjugates was prepared as described in Example 1 except that 3.2 g/L sodium chloride was added and trisodium EDTA was omitted.

EXAMPLE 3

Study of Gamma Globulin with Various Casein Concentrations

Tonsils were treated with fixative B5 (6% mercuric chloride, 1.25% sodium acetate, 4% formaldehyde) and embedded in paraffin. Microtome sections of the tonsils were affixed to both positively charged and uncharged glass slides and were tested on the Ventana 320 automated immunohistochemical stainer.

Slides with deparaffinized tissue sections were placed in the automated immunohistochemical stainer. There, each slide was rinsed with 8.5 ml wash solution (1.72 g/L 30% BRIJ 35 surfactant, 0.05 ml/L PROCLIN 300 antibiotic in 0.1M Tris, pH 7.6) of which approximately 300 μl remained on the slide above the tissue section. The tissue section with 300 μl of wash solution was then covered with 500 μl of pentadecane which acts as an evaporation inhibitor. The washing and addition of an evaporation inhibitor was performed in the same manner throughout the remainder of the procedure at the end of each incubation period.

The slides within the instrument were heated to 42° C., washed with wash solution and covered with evaporation inhibitor. The temperature was maintained at 42° C. for the remainder the procedure.

Next, 100 μl of endogenous peroxidase inhibitor (3% $H_2O_2$ in PBS, pH 7.3, 0.1% Tween 20 surfactant) was added to each slide by dropping the solution through the layer of evaporation inhibitor and into the 300 μl of wash solution above the tissue section. This solution was incubated for 4 minutes. The slides were rinsed with wash solution and covered with evaporation inhibitor.

Each slide received 100 μl of the diluent from Example 1 but lacking casein for a four minute incubation. The slides were rinsed with wash solution and covered with evaporation inhibitor.

The biotinylated secondary antibody solution (100 μl), 17.5 μg/ml biotinylated goat anti-mouse IgG (H+L), 7.5 μg/ml biotinylated goat anti-mouse IgM (μ chain specific), 7.5 μg/ml biotinylated goat anti-rabbit IgG (H+L) (all from Vector Laboratories, Inc., Burlingame, Calif.) in the diluent from Example 1 but containing either 0, 1.5, 3, 6 or 12 mg/ml casein, was added to each slide and incubated for 8 minutes. After incubation, the slides were rinsed with wash solution and the evaporation inhibitor was applied.

Peroxidase-labeled strepavidin (100 μl) (Southern Biotechnology Associates, Inc., Birmingham, Ala.) diluted 1:75 in the diluent from Example 2 but containing varying amounts of casein, was added to each slide and incubated for 8 minutes. For each slide, the concentration of casein in the peroxidase-labeled strepavidin solution was the same as it had been for the biotinylated secondary antibody solution. After incubation, the slides were rinsed with wash solution and the evaporation inhibitor was applied.

A diaminobenzidine solution (2 g/L diaminobenzidine in 7.5 mM citrate-phosphate buffer, pH 5.3, containing 1.0 mM sodium metabisulfite and 5% polyethylene glycol) (100 μl) was added to the slide. Then, 100 μl 0.02% $H_2O_2$ in PBS, pH 7.3, 0.1% Tween 20 surfactant was added and mixed with the diaminobenzidine solution to start the reaction. The mixture was incubated for 8 minutes.

The slides were rinsed. The evaporation inhibitor was applied, and then the diaminobenzidine color was enhanced with copper sulfate solution (0.5% $CuSO_4$ in 0.1M acetate buffer, pH 5.0, 0.1% Tween 20 surfactant) by incubating the solution for 4 minutes. Following the diaminobenzidine enhancement, the slide was rinsed but no evaporation inhibitor was applied.

The slides were removed from the instrument and the tissue was dehydrated (using alcohol/xylene) and coverslipped. The stained slides were visually inspected to determine the intensity of nonspecific staining with each of the formulations. The study demonstrated that nonspecific background decreased when casein was a component of both the avidin and biotin. The ideal concentration of casein in the biotin and avidin conjugate diluents was 12 mg/ml.

EXAMPLE 4

Study of Casein with Various Gamma Globulin Concentrations

The staining method was performed as described in Example 3 with the following exceptions. The biotin and avidin conjugates were present in a casein-containing (12 mg/ml) diluent, but the gamma globulin concentration varied. The two concentrations of gamma globulin that were added to the diluent and used in the staining procedure were 0 g/L and 3 g/L. The tissue used was frozen tonsil on uncharged glass slides and was chemically stained using Ventana's diaminobenzidine detection chemistry as described in Example 3. The primary antibody used was Ventana's Negative control for an incubation time of 16 minutes. The stained slides were analyzed to determine the amount of both non-specific and specific background staining with each of the formulations.

The study demonstrated that non-specific background as well as Fc receptor background decreased when gamma globulin was a component of both the avidin and biotin. The ideal concentration of gamma globulin in the biotin and avidin conjugate diluents was 3 g/L.

EXAMPLE 5

Staining of Tissue with Biotin/Avidin

In brief, the tissue sections used in this study were from frozen tonsil and from tonsil treated with neutral-buffered formalin (100 ml/L 40% formalin, 4 g/L monobasic sodium chloride monohydrate, 6.5 g/L anhydrous dibasic sodium phosphate) and embedded in paraffin. Tissue sections were affixed to positively charged or uncharged glass slides and were immunostained on the Ventana 320 automated immunohistochemical stainer with primary antibodies directed against CD45, CD15 or Factor VIII. Control tissue received no primary antibody. Antigen-primary antibody complexes were further detected using biotin-labeled secondary antibodies and streptavidin-enzyme conjugates. Both streptavidin-alkaline phosphatase conjugate and streptavidin-horseradish peroxidase conjugate were used. For the conjugate with horseradish peroxidase, hydrogen peroxide was the substrate and diaminobenzidine, the chromogen. For the conjugate with alkaline phosphatase, naphthol phosphate was the substrate and Fast Red KL, the chromogen.

Specifically, slides with frozen tonsil sections were dipped in ice cold acetone and dehydrated in a desiccator before being placed in the automated immunohistochemical stainer. Slides with paraffin-embedded tissue sections were deparaffinized. In the instrument, each slide was rinsed with wash solution and covered with evaporation inhibitor, as described in Example 3. In the instrument, the slides were heated to 42° C. and again, rinsed with wash solution and covered with evaporation inhibitor. The temperature was maintained at 42° C. for the remainder of the procedure.

All slides with formalin-fixed tonsil that were to be incubated with streptavidin-horseradish peroxidase, received 100 µl of endogenous peroxidase inhibitor as described in Example 3 which was incubated for 4 minutes. The slides were rinsed with wash solution and covered with evaporation inhibitor.

All slides with formalin-fixed tonsil to receive anti-Factor VIII primary antibody were treated for four minutes with 100 µl of solution containing 0.05 units of alkaline VIII protease (E.C. 3-4-21-14). The slides were rinsed with wash solution and covered with evaporation inhibitor.

Then, each slide received 100 µl of the appropriate primary antibody in diluent described in Example 1 but lacking casein, for a 32 minute incubation. The specificity, dilution, host, isotype, and vendor of the primary antibodies were: anti-CD45, 1:160, murine IgG monoclonal (Novocastra Laboratories Ltd., Newcastle upon Tyne, U.K.); anti-CD15, 1:15, murine IgM monoclonal (Becton Dickinson Inc., San Jose, Calif.); anti-Factor VIII, 1:4000, rabbit IgG polyclonal (Dako Corp., Carpinteria, Calif.). Neither antibody nor diluent was dispensed onto the control slides. At the end of the incubation, the slides were rinsed with wash solution and covered with evaporation inhibitor.

Then 100 µl biotinylated secondary antibody solution was added to each slide and incubated for 8 minutes. Biotinylated secondary antibody solution consisted of 15 µg/ml biotinylated goat anti-mouse IgG (H+L), 10 µg/ml biotinylated goat anti-mouse IgM (µ chain specific), 5 µg/ml biotinylated goat anti-rabbit IgG (H+L) (all from Vector Laboratories, Inc., Burlingame, Calif.) in the diluent of Example 1. After incubation, the slides were rinsed with wash solution and the evaporation inhibitor was applied.

Slides to be stained with diaminobenzidine received 100 µl horseradish peroxidase-streptavidin (Southern Biotechnology Associates, Inc., Birmingham, Ala.) diluted 1:75 in the diluent from Example 2, for an 8 minute incubation. Slides intended to be stained with Fast Red KL received 100 µl alkaline phosphatase-streptavidin (Tago Inc., Burlingame, Calif.) diluted 1:1600 in the diluent of Example 2, for a 12 minute incubation. After the incubation with the appropriate streptavidin-enzyme conjugate, the slides were rinsed with wash solution and the evaporation inhibitor was applied.

Those slides that had previously been incubated with streptavidin-peroxidase received 100 µl diaminobenzidine solution (see Example 3). In addition, 100 µl 0.02% $H_2O_2$ in PBS, pH 7.3, 0.1% Tween 20 was added and mixed with the diaminobenzidine solution to start the reaction. The mixture was incubated for 8 minutes. The slides were rinsed. The evaporation inhibitor was applied, and then the diaminobenzidine color was enhanced with copper sulfate solution (described in Example 3) by incubating the solution for 4 minutes. Following the diaminobenzidine enhancement, the slide was rinsed but no evaporation inhibitor was applied.

Those slides that had previously been incubated with streptavidin-alkaline phosphatase received 100 µl of 1.72 g/L 30% Brij 35, 0.5 ml/L ProClin 300 in 0.5M magnesium chloride, and four minutes later, 100 µl each of Fast Red KL solution (5 g/L 2-carbamoyl-5-methoxybenzene-diazonium chloride hemi[zinc chloride] salt, 12.32 g/L 30% BRIJ 35 surfactant, 0.5 ml/L PROCLIN 300 antibiotic, 0.58 ml/L glacial acetic acid in 0.245M magnesium chloride) and naphthol phosphate solution (7 g/L naphthol AS-TR phosphate, sodium salt (Sigma Chemical Co., Catalog No. N-6125), 7.5 g/L L-homoarginine, 1.5 g/L levamisole, in 0.5M Tris, pH 10). Eight minutes after that, another 100 µl of Fast Red KL solution was applied. Eight minutes after this last addition, the slides were rinsed but no evaporation inhibitor was applied.

The slides were removed from the instrument and the tissue was dehydrated (using alcohol/xylene) and coverslipped.

The slides were examined microscopically and special attention was given to evaluating both the intensity of specific staining and of nonspecific staining. Specific staining was uniformly high for all three isotypes of primary antibody, regardless of whether the tissue had been formalin-treated or frozen. Furthermore, the level of nonspecific staining was consistently low. When these slides were contrasted with slides that had been stained using the same primary antibodies but with casein-free biotinylated antibody solution and casein-free avidin-enzyme solution, it was evident that specific staining had been maintained while nonspecific staining had been significantly reduced.

What is claimed is:

1. A biotin-avidin formulation comprising a conjugate selected from the group consisting of a biotinylated antibody conjugate and an avidin-enzyme conjugate in a suitable diluent for immunohistochemical staining, said diluent additionally comprising:

(a) casein in an amount sufficient to prevent charge interactions of the conjugate with a tissue section; and
   (b) gamma globulin prepared from nonimmune serum in an amount sufficient to prevent Fc receptor binding and any hydrophobic interaction of the conjugate with a tissue section.

2. The formulation of claim 1 wherein casein is present at a concentration of from about 5 mg/ml to about 30 mg/ml.

3. The formulation of claim 2 wherein casein is present at a concentration of from about 10 mg/ml to about 15 mg/ml.

4. The formulation of claim 1 wherein the gamma globulin is present at a concentration of from about 1 mg/ml to about 50 mg/ml.

5. The formulation of claim 4 wherein the gamma globulin is present at a concentration of about 3 mg/ml.

6. The formulation of claim 1 wherein the conjugate is a biotinylated antibody.

7. The formulation of claim 6 wherein the antibody is selected from the group consisting of goat anti-rabbit IgG, goat anti-mouse IgG, and goat anti-mouse IgM.

8. The formulation of claim 6 wherein the gamma globulin is from the same species as the antibody.

9. The formulation of claim 1 wherein the conjugate is an avidin-enzyme conjugate.

10. The formulation of claim 9 wherein the enzyme is selected from the group consisting of horseradish peroxidase, alkaline phosphatase, and β-galactosidase.

11. A biotin-avidin detection system kit comprising:
   (a) in a first container, a biotinylated antibody conjugate; and
   (b) in a second container, an avidin-enzyme conjugate, wherein the biotinylated antibody conjugate and avidin-enzyme conjugate are each present in a suitable diluent for immunohistochemical staining comprising casein in an amount sufficient to prevent charge interactions of the conjugate with a tissue section and gamma globulin prepared from nonimmune serum in an amount sufficient to prevent Fc receptor binding and any nonspecific hydrophobic interaction of the conjugate.

12. The biotin-avidin detection kit of claim 11 wherein the antibody is a goat antibody.

13. The biotin-avidin detection kit of claim 11 wherein the gamma globulin is from the same species as the antibody.

14. The biotin-avidin detection kit of claim 11 wherein the kit additionally comprises, in a third container, a substrate for the enzyme of the avidin-enzyme conjugate.

\* \* \* \* \*